(12) United States Patent
Zhang et al.

(10) Patent No.: US 10,020,174 B2
(45) Date of Patent: Jul. 10, 2018

(54) METHODS AND DEVICES FOR PARALLEL ANALYSIS OF ION MOBILITY SPECTRUM AND MASS SPECTRUM

(71) Applicant: SHIMADZU CORPORATION, Kyoto-shi, Kyoto (JP)

(72) Inventors: Xiaoqiang Zhang, Shanghai (CN); Yunqing Huang, Shanghai (CN); Wenjian Sun, Shanghai (CN)

(73) Assignee: SHIMADZU CORPORATION, Kyoto-Shi, Kyoto (JP)

( * ) Notice: Subject to any disclaimer, the term of this patent is extended or adjusted under 35 U.S.C. 154(b) by 0 days.

(21) Appl. No.: 15/476,149

(22) Filed: Mar. 31, 2017

(65) Prior Publication Data
US 2017/0294295 A1 Oct. 12, 2017

(30) Foreign Application Priority Data
Apr. 8, 2016 (CN) .......................... 2016 1 0216645

(51) Int. Cl.
*H01J 49/00* (2006.01)
*G01N 27/62* (2006.01)

(52) U.S. Cl.
CPC .......... *H01J 49/009* (2013.01); *G01N 27/624* (2013.01); *H01J 49/005* (2013.01); *H01J 49/0036* (2013.01)

(58) Field of Classification Search
CPC .. G01N 27/624; H01J 49/009; H01J 49/0036; H01J 49/005
USPC ................................................ 250/281, 282
See application file for complete search history.

(56) References Cited

U.S. PATENT DOCUMENTS

| 8,785,848 B2 | 7/2014 | Wu et al. |
| 9,024,255 B2 | 5/2015 | Osgood et al. |
| 9,142,395 B2 | 9/2015 | Wu et al. |

OTHER PUBLICATIONS

Bilbao, Aivett et al., "Processing strategies and software solutions for data-independent acquisition in mass spectrometry", Proteomics, vol. No. 15: Issue 5-6, pp. 964-980, Accepted: Nov. 24, 2014.

(Continued)

*Primary Examiner* — Nicole Ippolito
*Assistant Examiner* — Hanway Chang
(74) *Attorney, Agent, or Firm* — Tim Tingkang Xia, Esq.; Locke Lord LLP

(57) ABSTRACT

A method for parallel analysis in mass spectrometry and ion mobility spectrometry includes enabling a sample to be subjected to a chromatography separation; ionizing the chromatography separated sample and then feeding the sample into a succeeding stage device for analysis, comprising: analyzing at least part of the ionized sample through an ion mobility spectrometer to obtain an ion mobility spectrum, and analyzing at least other parts of the sample through a mass spectrometer to obtain a mass spectrum, wherein the period for obtaining each ion mobility spectrum and each mass spectrum being not longer than 5 s; and performing data post-processing, comprising: correlating the peaks in said ion mobility spectrum and the peaks in said mass spectrum with a deconvolution algorithm according to the consistency in retention time or elution profile for the same analyte in said chromatography.

30 Claims, 4 Drawing Sheets

(56) References Cited

OTHER PUBLICATIONS

Shliaha, Pavel V. et al., "Effects of Traveling Wave Ion Mobility Separation on Data Independent Acquisition in Proteomics Studies", Journal of Proteome Research, vol. No. 12: Issue 6, pp. 2323-2339, Published: Mar. 20, 2013.

Distler, Ute et al., "Drift time-specific collision energies enable deep-coverage data-independent acquisition proteomics", Nature Methods, vol. No. 11: Issue 2, pp. 167-170, Feb. 2014.

METHODS AND DEVICES FOR PARALLEL ANALYSIS OF ION MOBILITY SPECTRUM AND MASS SPECTRUM

CROSS-REFERENCE TO RELATED APPLICATION

This application claims the priority to Chinese Patent Application No. N201610216645.8 filed on Apr. 8, 2016, in the State Intellectual Property Office of P.R. China, which is hereby incorporated herein in its entirety by reference.

FIELD OF THE INVENTION

The present invention relates generally to the field of ion analysis, and more particularly to methods and devices for parallel analysis in mass spectrometry and ion mobility spectrometry.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as the prior art against the present invention.

In recent years, technology to combine an ion mobility spectrometer and a chromatograph-mass spectrometer in a tandem use obtains a significant development. Due to an orthogonal separation characteristic of the ion mobility spectrometry to the chromatography and mass spectrometry, the separating power and the peak capacity of chromatography-mass spectrometry analysis can be greatly improved.

For a typical drift tube ion mobility spectrometer, for example, has a 1-4 torr gas pressure, a 50-100 cm length and a 2-5 kV drift voltage across the whole length, the drift time for most ions is in a millisecond scale, and the peak width in a spectrum is in millisecond or sub-millisecond scale. If the chromatograph, ion mobility spectrometer and mass spectrometer are connected serially, the speed of the ion mobility spectrometer can totally meet the request of the chromatography which is located on the pre-stage. But the speed of mass spectrometer, which is located on the succeeding stage of the ion mobility spectrometer, needs to be operated very fast to sampling the mobility peaks, usually only a high-speed time-of-flight mass spectrometer can be used herein. For other relatively low end mass analyzer, such as quadrupole mass filter or ion trap, it takes dozens or even hundreds of milliseconds to obtain a full scan spectrum, which is too slow to couple with an ion mobility spectrometer. The time-of-flight mass spectrometer needs a high vacuum and a long flight distance. Its size is relatively large and its price is high. In addition, a typical repetition rate of a time-of-flight mass spectrometer is 5-10 kHz, even though a sampling requirement for peaks in the mobility spectrometer can be met, it generates a massive data volume, and it brings difficulty in data processing and analyzing.

In order to overcome above shortcomings, a parallel analysis between ion mobility spectrometry and mass spectrometry can be performed, which means an ion mobility spectrum and a mass spectrum of the same sample are obtained simultaneously. For a complex sample, the difficulty of such technology is how to correlate the peaks in the ion mobility spectrum to those in the mass spectrum, i.e., how to obtain the ion mobility information and corresponding m/z information for the same component (or same ion). U.S. Pat. Nos. 8,785,848, 9,024,255 and 9,142,395 disclose a parallel analysis device and method. A typical process is as below: Performing a pre-scan to obtaining the ion mobility spectrum. According to the peak position to determine the time sequence for mass spectra acquisition, usually a vacuum valve will be open or closed accordingly. The time sequence decides a corresponding relation between the mass spectrum and the ion mobility spectrum, so that both the m/z information and ion mobility information for the analytes can be obtained at the same time. The method disclosed in the patents needs synchronization firstly and needs normalization secondly, the so-called normalization refers to correlation of peaks in the mobility spectrum and peaks in the mass spectrum according to a "synchronized" time sequence. The method disclosed in the patents cannot solve all problems in the aforesaid tandem analysis. In the patents, if such a quadrupole rod or ion trap analyzer is adopted, only the target analysis on known compounds can be performed, or the mass range needs to be reduced according to the peak position in the pre-scanned mobility spectrum. From this point, the method disclosed in the patents is not a complete parallel analysis. The process of this method is similar to "data dependent acquisition".

The so-called "data dependent acquisition (short for DDA)" or "data independent acquisition (short for DIA)" is usually applied in the field of tandem mass analysis, for example, as described in the literature, Proteomics 2015, 15, 964-980. In the DDA method, parent ions with a single m/z value are selected for collision dissociation to generate daughter ions, and then a mass analysis for those daughter ions is performed. In the DIA method, the parent ions in a certain m/z range, or even the entire range are selected, and are fed into a collision cell for dissociation to generate the daughter ions, then all daughter ions are subjected for mass analysis. A more complex data post-processing algorithm, usually called deconvolution, is necessary to correlate the daughter ions to the relevant parent ions. Compared to the DDA method, the DIA method has great superiority in its sensitivity, quantitation ability and dynamic range.

At present, the work to apply the DIA method to the ion mobility-mass spectrometry for a tandem analysis already existed. For example, there was a report in J. Proteome Res. 2013, 12, 2323-2339. In another literature, Nat. Methods 2014, 11, 167-170, it is further provided that the collision energy can be optimized according to the peak position of the mobility spectrum so as to obtain a higher dissociation efficiency to improve the qualitative and quantitative analysis capability.

But these methods are merely limited to serial (or tandem) analysis. There is no one who applies the DIA method to the ion mobility-mass spectrometry parallel analysis yet.

Therefore, a heretofore unaddressed need exists in the art to address the aforementioned deficiencies and inadequacies.

SUMMARY OF THE INVENTION

One aspect of the present invention provides a method parallel analysis in mass spectrometry and ion mobility spectrometry, comprising: enabling a sample to be subjected to a chromatography separation; ionizing the chromatography separated sample and then feeding the sample into a succeeding stage device for analysis, comprising: analyzing at least part of the ionized sample through an ion mobility spectrometer to obtain an ion mobility spectrum, and analyzing at least other parts of the sample through a mass spectrometer to obtain a mass spectrum, wherein the period for obtaining each ion mobility spectrum and each mass spectrum being not longer than 5 s; and performing data post-processing, comprising: correlating the peaks in said ion mobility spectrum and the peaks in said mass spectrum with a deconvolution algorithm according to the consistency in retention time or elution profile for the same analyte in said chromatography.

In one embodiment, the chromatography separated sample is divided into two paths by a switching valve before the ionization, and said two paths of samples are then ionized and respectively fed to the ion mobility spectrometer and the mass spectrometer for analysis.

In one embodiment, the chromatography separated sample is ionized, and generated ions are respectively transmitted to the ion mobility spectrometer and the mass spectrometer through two different ion inlets.

In one embodiment, the chromatography separated sample is ionized, and generated ions pass through an ion optical device, wherein said ion optical device periodically alternately feeds said ions to the ion mobility spectrometer and the mass spectrometer for analysis.

In one embodiment, the chromatography separated sample is ionized, and generated ions are separated by the ion mobility spectrometer and then are analyzed by the mass spectrometer.

In one embodiment, the chromatography is a gas chromatography, a liquid chromatography, a supercritical fluid chromatography, an ion chromatography or a capillary electrophoresis apparatus.

In one embodiment, the ion mobility spectrometer is a drift tube ion mobility spectrometer, a differential ion mobility spectrometer or a high-field asymmetric waveform ion mobility spectrometer (FAIMS).

In one embodiment, the mass analyzer of the mass spectrometer is a quadrupole mass filter or an ion trap mass analyzer, or a Fourier transform ion cyclotron resonance mass analyzer or an Orbitrap mass analyzer.

In one embodiment, the mass analyzer of the mass spectrometer is a time-of-flight mass analyzer.

In one embodiment, the mass spectrometer is a tandem mass spectrometer containing a collision cell.

In one embodiment, the chromatography separated sample is ionized, and generated ions enter the collision cell for collisional dissociation, and then pass through an ion optical device, wherein said ion optical device periodically alternately feeds said ions to the ion mobility spectrometer and the mass spectrometer for analysis.

In one embodiment, after the chromatography separation and ionization for sample, and then being collisional dissociated in said collision cell, the generated ions are separated by the ion mobility analyzer in the ion mobility spectrometer, and then enter the mass analyzer in the mass spectrometer for mass analysis.

In one embodiment, after the chromatography separation and ionization for sample, the generated ions are separated by the ion mobility analyzer in the ion mobility spectrometer, then enter the collision cell for collisional dissociation, and then the generated ions enter the mass analyzer in the mass spectrometer for mass analysis.

In one embodiment, the deconvolution algorithm is one or a combination of more of a Pearson's correlation coefficient algorithm, a cross correlation score algorithm, a clustering algorithm, an entropy minimization algorithm, a Dot product score algorithm and a minimum spanning tree algorithm.

In one embodiment, the data post-processing further comprises: performing charge number deconvolution on the mass spectrum to determine a charge number corresponding to a mass spectrum peak.

Another aspect of the present invention provides a device for parallel analysis in mass spectrometry and ion mobility spectrometry, comprising: a chromatograph; an ion mobility spectrometer located at a succeeding stage of the chromatograph; a mass spectrometer located at a succeeding stage of the chromatography; and a computer connected to the ion mobility spectrometer and the mass spectrometer, wherein a sample is subjected to a chromatography separation; the chromatography separated sample is ionized and then fed into a succeeding stage device for analysis, comprising: analyzing at least part of the ionized sample through an ion mobility spectrometer to obtain an ion mobility spectrum, and analyzing at least other parts of the sample through a mass spectrometer to obtain a mass spectrum, wherein the period for obtaining each ion mobility spectrum and each mass spectrum being not longer than 5 s; the computer performs data post-processing, comprising: correlating the peaks in said ion mobility spectrum and the peaks in said mass spectrum with a deconvolution algorithm according to the consistency in retention time or elution profile for the same analyte in said chromatography.

In one embodiment, the device further comprises at least one switching valve, connected to the chromatography, wherein, the chromatography separated sample is divided into two paths by the switching valve before the ionization, and said two paths of samples are then ionized and respectively fed to the ion mobility spectrometer and the mass spectrometer for analysis.

In one embodiment, the device further comprises two different ion inlets respectively connected to the ion mobility spectrometer and the mass spectrum analyzer, wherein the chromatography separated sample is ionized, and generated ions are respectively transmitted to the ion mobility spectrometer and the mass spectrometer through two different ion inlets.

In one embodiment, the device further comprises an ion optical device, wherein the chromatography separated sample is ionized, and generated ions pass through the ion optical device, wherein said ion optical device periodically alternately feeds said ions to the ion mobility spectrometer and the mass spectrometer for analysis.

In one embodiment, the chromatography separated sample is ionized, and generated ions are separated by the ion mobility spectrometer and then are analyzed by the mass spectrometer.

In one embodiment, the chromatography is a gas chromatography, a liquid chromatography, a supercritical fluid chromatography, an ion chromatography or a capillary electrophoresis apparatus.

In one embodiment, the ion mobility spectrometer is a drift tube ion mobility spectrometer, a differential ion mobility spectrometer or a high-field asymmetric waveform ion mobility spectrometer (FAIMS).

In one embodiment, the mass analyzer of the mass spectrometer is a quadrupole mass filter or an ion trap mass analyzer, or a Fourier transform ion cyclotron resonance mass analyzer or an Orbitrap mass analyzer.

In one embodiment, the mass analyzer of the mass spectrometer is a time-of-flight mass analyzer.

In one embodiment, the mass spectrometer is a tandem mass spectrometer containing a collision cell.

In one embodiment, the chromatography separated sample is ionized, and generated ions enter the collision cell for collisional dissociation, and then pass through an ion optical device, wherein said ion optical device periodically alternately feeds said ions to the ion mobility spectrometer and the mass spectrometer for analysis.

In one embodiment, after the chromatography separation and ionization for sample, and then being collisional dissociated in said collision cell, the generated ions are separated by the ion mobility analyzer in the ion mobility spectrometer, and then enter the mass analyzer in the mass spectrometer for mass analysis.

In one embodiment, after the chromatography separation and ionization for sample, the generated ions are separated by the ion mobility analyzer in the ion mobility spectrometer, then enter the collision cell for collisional dissociation, and then the generated ions enter the mass analyzer in the mass spectrometer for mass analysis.

In one embodiment, the deconvolution algorithm is one or a combination of more of a Pearson's correlation coefficient algorithm, a cross correlation score algorithm, a clustering algorithm, an entropy minimization algorithm, a Dot product score algorithm and a minimum spanning tree algorithm.

In one embodiment, the data post-processing further comprises: performing charge number deconvolution on the mass spectrum to determine a charge number corresponding to a mass spectrum peak.

As abovementioned, according to the method and device in mass spectrometry and ion mobility spectrometry provided by the present invention, a sample is separated by a chromatography; the chromatography separated sample is ionized and then fed into a succeeding stage device for analysis, comprising: analyzing at least part of the ionized sample through an ion mobility spectrometer to obtain an ion mobility spectrum, and analyzing at least other parts of the sample through a mass spectrometer to obtain a mass spectrum, wherein the period for obtaining each ion mobility spectrum and each mass spectrum being not longer than 5 s; The data post-processing is performed, comprising: correlating the peaks in said ion mobility spectrum and the peaks in said mass spectrum with a deconvolution algorithm according to the consistency in retention time or elution profile for the same analyte in said chromatography. The invention greatly reduces the request in acquisition speed to a mass spectrometer if coupling with an ion mobility spectrometer. It also greatly reduces the data volume.

The key of the present invention is to perform deconvolution on signals of chromatography effluxes detected by the mass spectrometer and the ion mobility spectrometer together through a mathematical treatment method, such that the ion mobility and m/z information of each analyte are combined to obtain multidimensional information. Compared with the prior art, the present invention has the following advantages:

1. The invention greatly reduces the request in acquisition speed to a mass spectrometer if coupling with an ion mobility spectrometer. Since it is okay as long as the acquisition speed of the mass spectrometer can follow up the chromatography elution, almost all current types of mass analyzers including a quadrupole and ion trap mass analyzer can be used. The instrument can be with a low cost or a small footprint.

2. The invention effectively reduces the data volume of analysis. Even using a high speed time-of-flight mass spectrometer, compared to the traditional method, only a mass spectrum accumulated through a second scale (instead of millisecond scale) needs to be saved, and therefore a data volume can be reduced by two to three orders of magnitudes.

3. The invention has wide applicability. Since the analysis is in parallel, there is no limitation to chromatographic variety, the mass analyzer variety, or the variety of the ion mobility analyzer. Advantages when each type of analyzer (or separator) is used can be maintained without performance compromising, in contrast, it is usually an issue in the traditional method when coupling a certain type of mass analyzer with an ion mobility analyzer.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
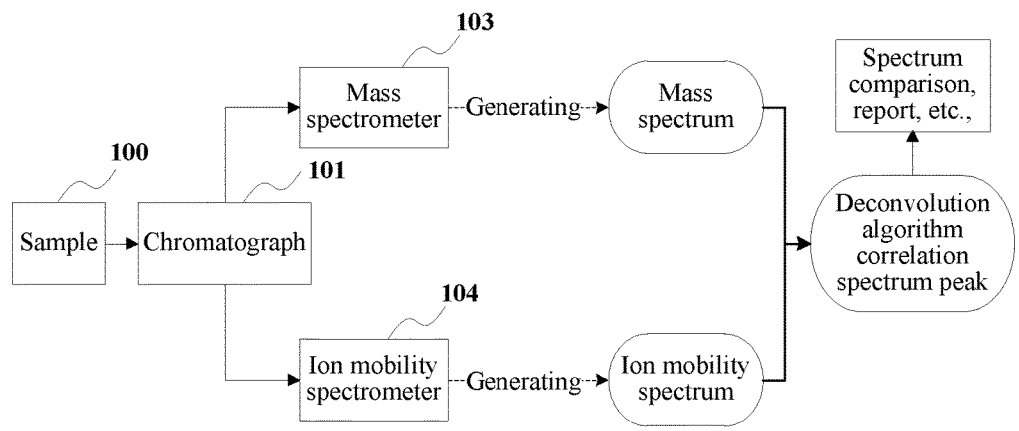
FIG. 1 shows a schematic diagram for the workflow of the parallel analysis in ion mobility spectrometry and mass spectrometry in a first embodiment of the present invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term are the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present there between. In contrast, when an element is referred to as being "directly on" another element, there are no intervening elements present. As used herein, the term "and/or" includes any and all combinations of one or more of the associated listed items. As used herein, the singular forms "a", "an" and "the" are intended to include the plural forms as well, unless the context clearly indicates otherwise.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

It should be noted that the structures, proportions and sizes shown in the drawings of the present invention are all used for matching with the content disclosed by the specification to allow those familiar with the prior art to learn and read rather than limiting executable limiting conditions of the present invention, and thus do not have any substantial meaning technologically, and any structural modification, proportional relation change or size adjustment should fall within a range that the technical content disclosed in the present invention can cover without influencing the effects generated and the achieved objectives by the present invention. Meanwhile, words such as "upper", "lower", "left", "right" and "one" referred in the present specification are merely intended for convenience of description rather than limiting an implementing range of the present invention, and the change or adjustment of a relative relation should be deemed to be in an implementing range of the present invention without essentially changing the technical content.

Furthermore, relative terms, such as "lower" or "bottom" and "upper" or "top", may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower" can, therefore, encompass both an orientation of "lower" and "upper", depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprise" or "comprising", "include" or "including", "carry" or "carrying", "has/have" or "having", "contain" or "containing", "involve" or "involving" and the like are to be open-ended, i.e., to mean including but not limited to, and when used in the claims and specification specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about", "substantially" or "approximately" can be inferred if not expressly stated.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

The description is now made as to the embodiments of the invention in conjunction with the accompanying drawings. In accordance with the purposes of this invention, as embodied and broadly described herein, this invention relates to methods and devices for parallel analysis of ion mobility spectrum and mass spectrum.

FIG. 1 shows a schematic diagram for the workflow of the parallel analysis in ion mobility spectrometry and mass spectrometry in a first embodiment of the present invention. The workflow comprises: after the pretreatment to a sample 100 which is ready to be analyzed, performing chromatography separation through a chromatograph 101; then dividing the sample into two paths which respectively enter a mass spectrometer 103 and an ion mobility spectrometer 104 for performing mass analysis and ion mobility analysis respectively to obtain a mass spectrum and an ion mobility spectrum respectively; then performing data post-processing, correlating the peaks in the ion mobility spectrum to those in the mass spectrum with a deconvolution algorithm according to the consistency in retention time or elution profile for the same analyte in said chromatograph, wherein the data post-processing can be finished by a computer.

In this flow, it only needs to be ensured that the period for obtaining each ion mobility spectrum and each mass spectrum being shorter than 5 s, and typically shorter than 2 s, that is, a sampling point number requirement on a chromatographic peak is ensured, in this way, the accuracy of an extracted ion current (XIC) chromatographic peak form of each spectrum peak (mass peak or ion mobility peak) can be ensured.

Without intent to limit the scope of the invention, hereinafter, FIGS. 2-5 are taken as examples for specific explanation.

Figure 2:
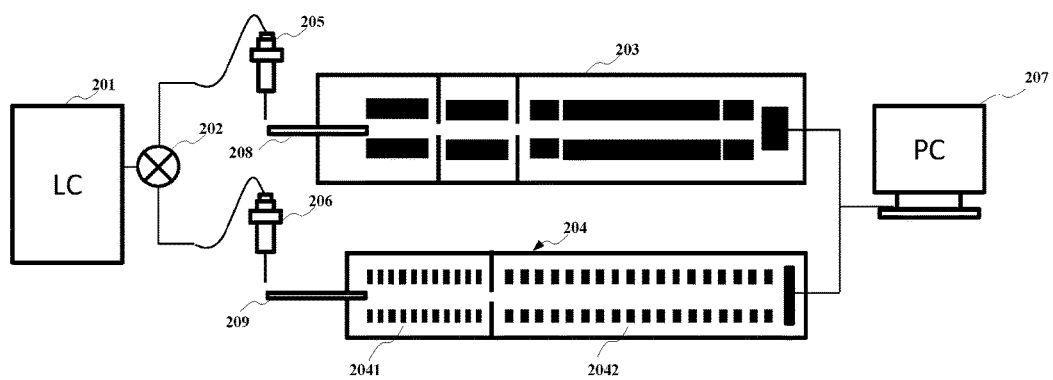
FIG. 2 shows a structural schematic diagram for one example of the parallel analysis in ion mobility spectrometry and mass spectrometry in the first embodiment of the present invention.

In FIG. 2, the sample is separated by a liquid chromatograph 201 (LC), the separated sample passes by a valve 202 which can be a split valve or a quick switching six-way valve, which aims to cause the well separated sample to respectively enter the mass spectrometer 203 and the ion mobility spectrometer 204. The so-called "respectively enter" needs to meet a condition that in each sampling point in a elution peak of the chromatography (the period is one tenth to one twentieth of the chromatographic peak and usually is smaller than 2 s), a part of sample passes by the mass spectrometer 203 and a part of sample passes by the ion mobility spectrometer 204. Hence a split valve can totally meet the requirement. If a switching valve is adopted, then its switching frequency is not slower than 1. In the present embodiment, typically, the mass spectrometer 203 and the ion mobility spectrometer 204 are respectively of a quadrupole mass filter and a drift tube ion mobility spectrometer. Independent ion sources 205 and 206 are adopted for the mass spectrometer 203 and the ion mobility spectrometer 204, and ions generated by the ion source 205 enter a first ion guide and a second ion guide through a vacuum interface 208, and then enter the quadrupole mass filter 203 for mass analysis to obtain a mass spectrum; and ions generated by the ion source 206 enter a desolvation chamber 2041 of the ion mobility spectrometer 204 through another vacuum interface 209 and then enter a drift tube 2042 for mobility analysis to obtain an ion mobility spectrum, and further data post-processing is performed in the computer 207.

Figure 3:
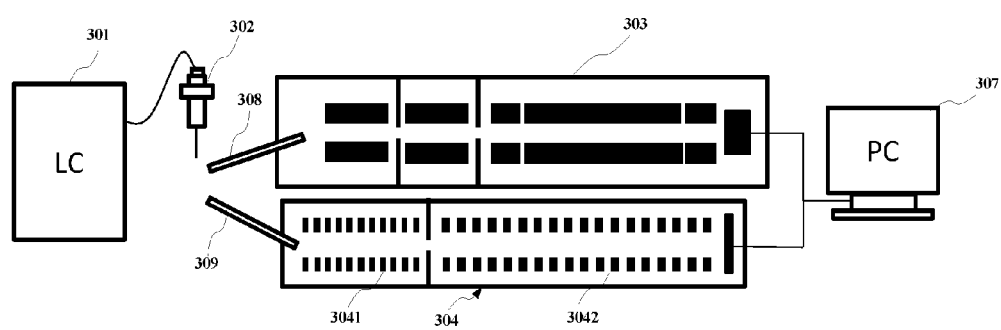
FIG. 3 shows a structural schematic diagram for another example of the parallel analysis in ion mobility spectrometry and mass spectrometry in the first embodiment of the present invention.
Figure 4:
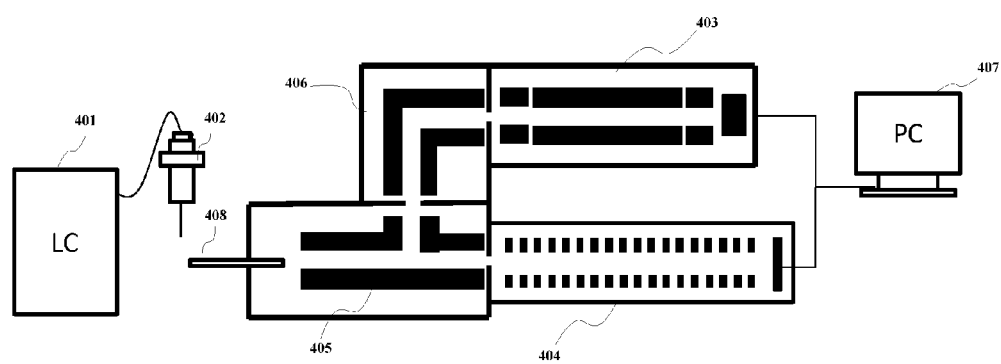
FIG. 4 shows a structural schematic diagram for yet another example of the parallel analysis in ion mobility spectrometry and mass spectrometry in the first embodiment of the present invention.
Figure 5:
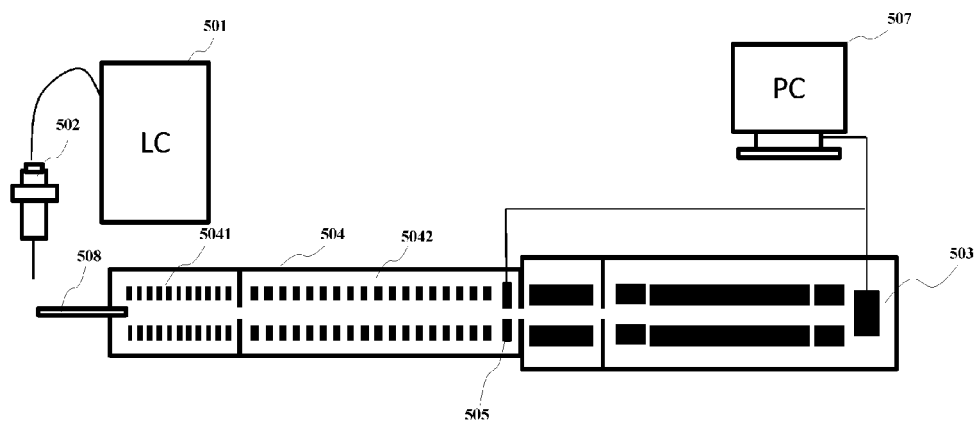
FIG. 5 shows a structural schematic diagram for yet another example of the parallel analysis in ion mobility spectrometry and mass spectrometry in the first embodiment of the present invention.

In other embodiments, if the same ion source is adopted, then the valve 202 is not required. FIGS. 3-5 give three different embodiments. As shown in FIG. 3, an ion source 302 connected to the chromatograph 301 generates massive ions, which enter the mass spectrometer 303 and the ion mobility spectrometer 304 through two different vacuum interfaces 308 and 309 (two capillaries herein) respectively, analysis is performed to obtain two spectra, and the data post-processing is performed on the computer 307. One is as shown in FIG. 4, the ions generated by an ion source 402 connected to the chromatograph 401 enter an ion guide device 405 through a vacuum inlet 408, such ion guide device 405 can be a T-shaped (or Y-shaped) ion guide, a specific structure can be a T-shaped (or Y-shaped) distributed segmented multipole rods, its T-shaped or Y-shaped middle end can be connected to one of the ion mobility spectrometer 404 or mass spectrometer 403 through a deflection ion guide device 406, one of two opposite ends is connected to the other of the ion mobility spectrometer 404 or mass spectrometer 403, the present embodiment only illustrates an embodiment that the middle end is connected to the mass spectrometer 403, but is not limited thereto; this ion guide device 405 can periodically change an ion transmission path, in a period of time, the ions are transmitted to enter the ion mobility analyzer in the ion mobility spectrometer 404 for analysis and obtaining an ion mobility spectrum, and in a period of time, the ions are transmitted to enter the ion mass analyzer in the mass spectrometer 403 for analysis and obtaining a mass spectrum. The two different transmission paths can be switched at a high speed (millisecond even microsecond scale), and the duration on two acquisition manners can be set in advance. For example, switching is performed twice in 1 s, wherein 100 ms is used for ion mobility analysis and rest 900 ms is used for mass analysis, finally, the data post-processing is performed on a computer 407. Another embodiment is as shown in FIG. 5, the mass analyzer in the mass spectrometer 503 is placed at a succeeding stage of the ion mobility analyzer in the ion mobility spectrometer 504, while a detector 505 of the ion mobility analyzer is of a ring electrode having a through hole, when the detector 505 is in a working state (for example, a very high negative voltage is applied), the ions can hit the detector 505, and when in a non-working state, the ions will enter the mass analyzer of the mass spectrometer 503 of the succeeding stage through the detector 505. The detector 505 is quickly switched between the working state and the non-working state, for example, is switched twice in 1 s, works for 100 ms for obtaining an ion mobility spectrum and does not work in rest 900 ms and can obtain a mass spectrum at the succeeding stage, and finally, data post-processing is performed on the computer 507.

The workflow that the present invention obtains the ion mobility spectrum and the mass spectrum is described above. The workflow for data post-processing is described hereinafter. A key of the present invention is to adopt a deconvolution algorithm to correlate or correspond the peaks in the ion mobility spectrum and peaks in the mass spectrum. Such algorithm has been widely applied in a DIA method, and is used for correlating parent ions and daughter ions. Generally, in the present invention, peaks in the ion mobility spectrum can be treated as those for "parent ions", and peaks in the mass spectrum can be treated as those of "daughter ions". Therefore, a similar method in the DIA can be suitable for the present invention. A common algorithm includes but not limited to a Pearson's correlation coefficient algorithm, a cross correlation score algorithm, a k-means clustering algorithm, an entropy minimization method, a Dot product score algorithm, a minimum spanning tree algorithm, etc. The above algorithms use retention time information of components in chromatography or use the information of elution peak profile in the chromatography, or use both.

A concept of the retention time is a basic chromatographic concept. The so-called elution peak profile means that when chromatography and mass spectrometry are combined for use, the intensity of the ion mobility peak corresponding to a single chromatographic elution is changed along with a concentration of the eluted analyte, and further one or more chromatographic profiles are presented in a whole chromatography separation time range; and similarly, the intensity change of the singe mass peak in the whole chromatography separation time range also presents one or more chromatographic profiles.

By taking the Pearson's correlation coefficient algorithm as an example, an intensity change of the chromatographic peak corresponding to the ion mobility peak is considered as an ordered vector; similarly, an intensity change of the chromatographic peak corresponding to the mass peak in the same chromatographic retention time range can also be considered as an ordered vector, a similarity between the two chromatography can be estimated by calculating a Pearson's correlation coefficient between these two ordered vectors, if the similarity is higher (more than a certain threshold), then the ion mobility peak and the mass peak are considered to have a corresponding relation. The corresponding relations between all ion mobility peaks and the mass peaks can be found out by above calculation for multiple times.

By taking the cross correlation score algorithm as an example, the chromatographic peaks corresponding to the ion mobility peaks and the chromatographic peaks corresponding to the mass peaks are grouped according to a difference of chromatographic peak retention time, two types of chromatographic peaks having the same retention time are divided into one group, and each group can contain one or more chromatographic peaks corresponding to the ion mobility peaks and one or more chromatographic peaks corresponding to the mass peaks. A cross correlation score between the chromatographic peaks in the group is calculated and the chromatographic peaks of which the cross correlation score of multiple chromatographic peaks in the group is smaller than a preset threshold are removed as a noise.

By taking a combination of multiple algorithms as an example, all mass peaks corresponding to certain ion mobility peaks are obtained through the above Pearson's correlation coefficient algorithm. These mass peaks have two characteristic parameters, one is retention time of the chromatographic peaks corresponding to the mass peaks, and the other is a Pearson's correlation coefficient between the chromatographic peaks corresponding to the mass peaks and between the chromatographic peaks corresponding to the ion mobility peaks. According to these two characteristic parameters, these mass peaks are clustered and analyzed by using a clustering algorithm, the mass peaks are divided into a plurality of clusters, one cluster with the highest Pearson's correlation coefficient at a mass center of the cluster is selected, and the mass peaks located in such cluster serve as preferable mass peaks corresponding to the ion mobility peaks. The multiple algorithms are combined for deconvolution, such that deconvolution effectiveness can be improved and occurrence of interference peaks is reduced.

The above is the data post processing process in the present invention. If multi-charge ions are contained, for example, during protein or peptide analysis, the multi-charge ions will be generated in electrospray ionization, an additional charge deconvolution algorithm can be used to determine a charge state. The additional algorithm processing can be before or after the data post-processing. In such a way, a charge number of each mass peak in the spectrum is determined, and thus a molecular weight is determined. The charge deconvolution process is not related to the deconvolution process of the present invention, but after the charge state of the mass peaks is determined, the charge state of the ion mobility peaks can also be determined according to the correlation. To combine the information in chromatographic retention time, ion charge number, molecular weight and ion mobility can greatly improve a qualitative and quantitative analysis capability.

It can be seen that in the present invention, obtaining of the mass spectrum is independent from that of the ion mobility spectrum, and the two are only correlated in later data processing. Therefore, requirements in aspects of instrument speed and data acquisition, etc., are greatly reduced. The chromatographs (101, 201, 301, 401 or 501) used above can be a gas chromatography, a liquid chromatography, a supercritical fluid chromatography or an ion chromatography, but can also be extended to other analysis means which have a separation capability and can be combined with the ion mobility spectrometer and mass spectrometer for use, for example, capillary electrophoresis, thin-layer chromatography, and paper chromatography. The mass analyzer in the mass spectrometer used above can be a high-speed time-of-flight mass spectrometer and can also be a relatively low-speed quadrupole mass filter, ion trap, Fourier transform ion cyclotron resonance mass spectrometry (FT-ICR), an Orbitrap and the like as long as it is ensured that the obtained mass spectrum number meets the requirements of chromatographic sampling points. The ion mobility spectrum analyzer used above can be an drift tube ion mobility spectrometer, and can also be a differential ion mobility spectrometer (DMA) and a high-field asymmetric waveform ion mobility spectrometer (FAIMS or DMS), etc., as long as it is ensured that the obtained ion mobility spectrum number meets the requirements of chromatographic sampling points. Therefore, the invention realizes true parallel analysis of the ion mobility spectrometry and the mass spectrometry, which is not realized in conventional technologies. Besides, the invention can keep the advantages when each type of analyzer (for example, ion mobility spectrometer and mass spectrometer) is singly used, and avoids performance compromising required for mutual matching. For example, in the conventional methods, when a drift tube and a time-of-flight mass spectrometer are serially used, an additional drift time of the ions at the succeeding stage of the drift tube will reduce a resolution of the ion mobility to certain extent, so that a more complex correction process is usually required. In the present invention, the ion mobility spectrometer works independently, and there are no needs for additional correction to assure its resolution. In the other aspect, when in tandem use with the ion mobility spectrometer, there is usually no ion bunching or trapping before the flight tube in a time-of-flight mass spectrometer, otherwise the ion mobility resolution will be damaged. However, the sensitivity will be reduced without ion bunching or trapping. In the present invention, ion bunching or ion trapping can be performed to ensure high sensitivity.

It needs to be pointed out that the so-called parallel analysis merely means that a data acquisition process is parallel or can be repeatedly performed. While the relative placing between analyzers can be diversified. For example, they can be placed in parallel as in FIGS. 2 and 3, or they can be in the T-shaped (or Y-shaped) as in FIG. 4, or they can be in a manner similar to a tandem configuration as in FIG. 5. It needs to be noted that in FIG. 5, the working manner is still performed in parallel (or alternately), that is, part of the ions is subjected to mass analysis and part of the ions is subjected to ion mobility analysis.

Figure 6:
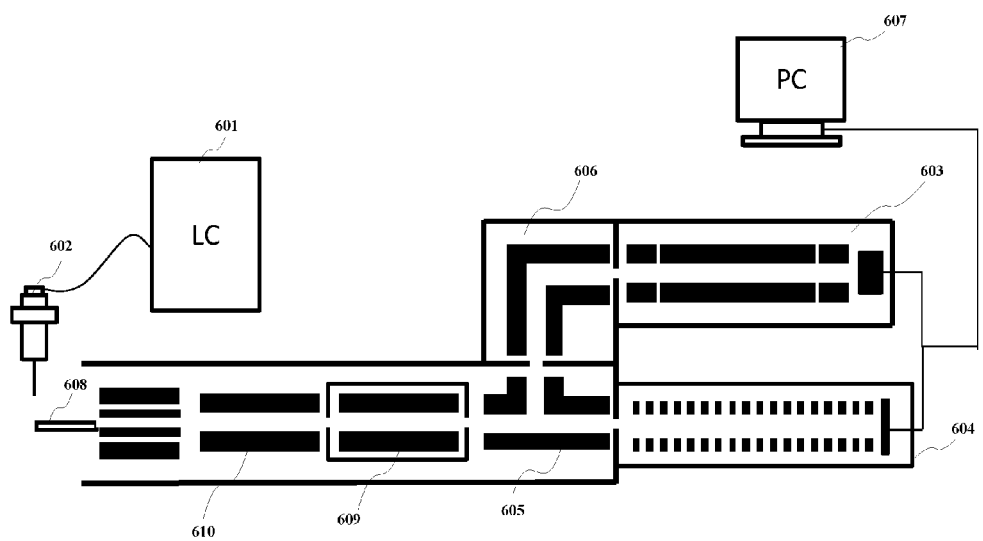
FIG. 6 shows a structural schematic diagram for one example of the parallel analysis in ion mobility spectrometry and mass spectrometry which is applied to tandem mass analysis in the first embodiment of the present invention.

The invention is also suitable for tandem mass analysis (MS/MS), as well as suitable for all means realizing tandem mass analysis. For example, dissociation in an ion trap, collision induced dissociation (CID), electron capture dissociation (ECD), electron transfer dissociation (ETD), infrared multiphoton dissociation (IRMPD), etc. Taken the CID as an example, there are two manners: one manner is that the collision cell is placed in the mass spectrometer, and is unrelated to the ion mobility spectrometer. If a parent ion scanning is adopted in the mass spectrometer, the peaks in the ion mobility spectrum and those of the parent ions in the mass spectrum can be correlated. If a daughter ion scanning is adopted, the peaks for the parent ion in the ion mobility spectrum and those of the daughter ions in the mass spectrum are correlated, but ion mobility information of the daughter ions cannot be obtained from this manner. The other manner is as shown in FIG. 6. The collision cell 609 is placed at the preceding stage of the ion mobility spectrometer 604 and the mass spectrometer 603. The ions enter the collision cell 609 from the ion guide device 610 at the preceding stage and are disassociated in the collision cell 609. Preferably, through the T-shaped (Y-shaped) ion guide device 605, part of ions enters the mass spectrometer 603 for mass analysis through the deflection ion guide device 606, and other part of ions enters the ion mobility spectrometer 604 from 605 for ion mobility analysis. Data post-processing is performed at the computer 607, so that ion mobility and mass information of the daughter ions can be obtained at the same time. If no CID is performed, then ion mobility and mass information of the parent ions can be obtained.

Figure 7:
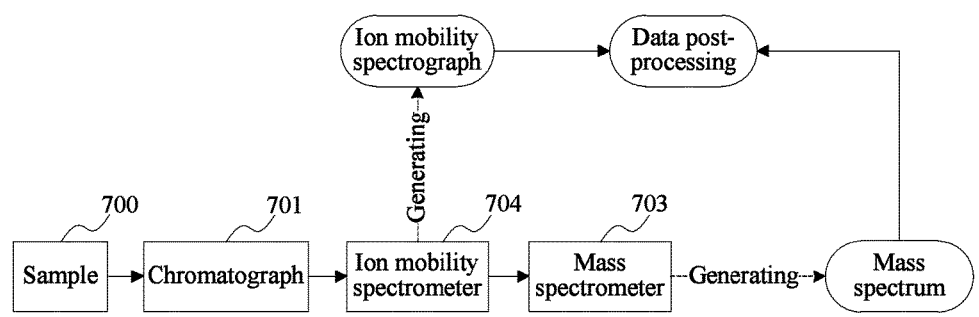
FIG. 7 shows a schematic diagram for the workflow of the parallel analysis in ion mobility spectrometry and mass spectrometry in a first embodiment in a second embodiment of the present invention.

Further, a schematic diagram for the workflow in the second embodiment of the present invention is as shown in FIG. 7. In this manner, the data acquisition process may not be in parallel, that is, a traditional chromatography-ion mobility spectrometry-mass spectrometry configuration can be adopted. In this configuration, a sample 700 passes through a chromatograph 701, an ion mobility spectrometer 704 and a mass spectrometer 703 sequentially to obtain an ion mobility spectrum and a mass spectrum. The data post-processing process described by the present invention can then be adopted. The deconvolution algorithm is to correlate the peaks of the ion mobility spectrum and those in the mass spectrum. Therefore, these peaks in two spectra do not need to be correlated from "hardware" according to a time sequence relation. This situation can be considered as a special "parallel" analysis. Anyway, such a device and a method also fall within a protective scope of the present invention.

Figure 8:
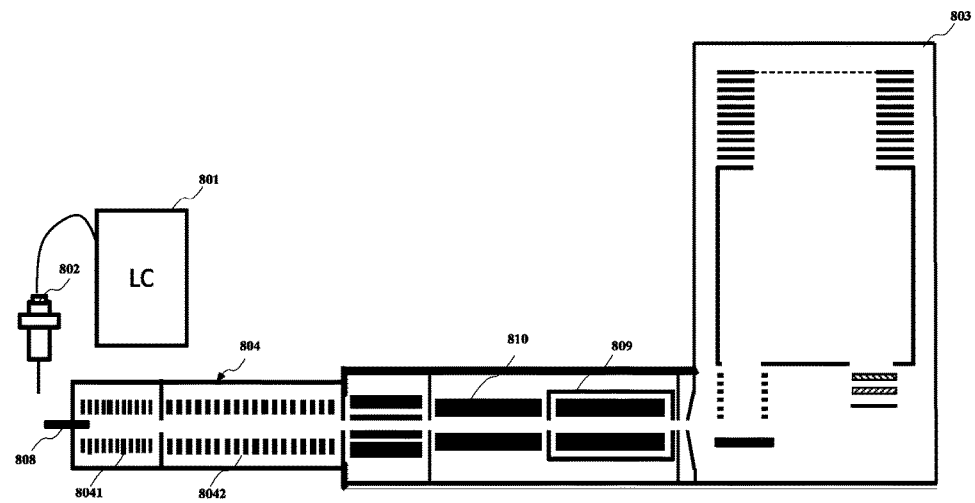
FIG. 8 shows a structural schematic diagram for one example of the parallel analysis in ion mobility spectrometry and mass spectrometry in the second embodiment of the present invention.

FIG. 8 gives an example of a second embodiment of the present invention to explain superiority of such a special parallel analysis manner. The embodiment implements a traditional chromatography-ion mobility spectrometry-time-of-flight mass spectrometry configuration. The only difference from the traditional method is the data processing process. In a traditional and typical workflow, the sample is firstly subjected to liquid chromatography separation through a chromatograph 801, then is ionized by an electrospray ion source 802 to generate ions. The ions enter a desolvation chamber 8041 of the ion mobility spectrometer 804 through an atmospheric interface, and then are separated according to the ion mobility in a drift tube 8042. The ions in each peak of ion mobility spectrum enter the collision cell 809 through the ion guide device 810 at the preceding stage, in which daughter ions can be generated by collisions or only the parent ions are transmitted without collisions. No tandem mass analysis is not considered here. All the ions will enter the mass spectrometer 803, which is a time-of-flight mass spectrometer in the present embodiment, for mass analysis. Since the speed of the time-of-flight mass spectrometer is very fast, usually it ensures that enough sampling points (1 point per millisecond for instance) for each mobility peak in the spectrum to can obtain corresponding mass spectra. Traditionally there is no need to re-correlate the peaks since the time sequence has been made certain. The problem is the data volume is very large. If the data size of a mass spectrum is 100 kb, about 100 Mb data needs to be recorded in one second. However, the method of the present invention can address the issue. In this method, a same workflow is still adopted, that is, the ions are separated by a drift tube firstly, and are then subjected to mass analysis through the time-of-flight mass spectrometer. Herein preferably, a pre-processing to spectra can be performed, in which we sum all the original mass spectra. For example, 1000 spectra which are obtained in 1 second can be summed firstly. Then the original 1000 mass spectra are thrown away and only the sum spectrum is saved. This process is performed in real time, but not a post data-processing. It can be finished in an FPGA for instance. After the pre-processing, we temporarily lose the correlation between the mass peaks and the ion mobility peaks. But the data volume is greatly reduced. For example, the data can be reduced by three orders of magnitudes after 1000 spectra are summed to be a spectrum. And then data post-processing is performed, in which the deconvolution algorithm is used to re-correlate the peaks in the summed mass spectrum and those in the ion mobility spectrum.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A method for parallel analysis in mass spectrometry and ion mobility spectrometry, comprising:
    enabling a sample to be subjected to a chromatography separation;
    ionizing the chromatography separated sample and then feeding the sample into a succeeding stage device for analysis, comprising: analyzing at least part of the ionized sample through an ion mobility spectrometer to obtain an ion mobility spectrum, and analyzing at least other parts of the sample through a mass spectrometer to obtain a mass spectrum, wherein the period for obtaining each ion mobility spectrum and each mass spectrum being not longer than 5s; and
    performing data post-processing, comprising: correlating the peaks in said ion mobility spectrum and the peaks in said mass spectrum with a deconvolution algorithm according to the consistency in retention time or elution profile for the same analyte in said chromatography.

2. The method of claim 1, wherein, the chromatography separated sample is divided into two paths by a switching valve before the ionization, and said two paths of samples are then ionized and respectively fed to the ion mobility spectrometer and the mass spectrometer for analysis.

3. The method of claim 1, wherein the chromatography separated sample is ionized, and generated ions are respectively transmitted to the ion mobility spectrometer and the mass spectrometer through two different ion inlets.

4. The method of claim 1, wherein the chromatography separated sample is ionized, and generated ions pass through an ion optical device, wherein said ion optical device periodically alternately feeds said ions to the ion mobility spectrometer and the mass spectrometer for analysis.

5. The method of claim 1, wherein the chromatography separated sample is ionized, and generated ions are separated by the ion mobility spectrometer and then are analyzed by the mass spectrometer.

6. The method of claim 1, wherein the chromatography is a gas chromatography, a liquid chromatography, a supercritical fluid chromatography, an ion chromatography or a capillary electrophoresis apparatus.

7. The method of claim 1, wherein the ion mobility spectrometer is a drift tube ion mobility spectrometer, a differential ion mobility spectrometer or a high-field asymmetric waveform ion mobility spectrometer (FAIMS).

8. The method of claim 1, wherein the mass analyzer of the mass spectrometer is a quadrupole mass filter, an ion trap mass analyzer, a Fourier transform ion cyclotron resonance mass analyzer or an Orbitrap mass analyzer.

9. The method of claim 1, wherein the mass analyzer of the mass spectrometer is a time-of-flight mass analyzer.

10. The method of claim 1, wherein the mass spectrometer is a tandem mass spectrometer containing a collision cell.

11. The method of claim 10, wherein the chromatography separated sample is ionized, and generated ions enter the collision cell for collisional dissociation, and then pass through an ion optical device, wherein said ion optical device periodically alternately feeds said ions to the ion mobility spectrometer and the mass spectrometer for analysis.

12. The method of claim 10, wherein after the chromatography separation and ionization for sample, and then being collisional dissociated in said collision cell, the generated ions are separated by the ion mobility analyzer in the ion mobility spectrometer, and then enter the mass analyzer in the mass spectrometer for mass analysis.

13. The method of claim 10, wherein after the chromatography separation and ionization for sample, the generated ions are separated by the ion mobility analyzer in the ion mobility spectrometer, then enter the collision cell for collisional dissociation, and then the generated ions enter the mass analyzer in the mass spectrometer for mass analysis.

14. The method of claim 1, wherein the deconvolution algorithm is one or a combination of more of a Pearson's correlation coefficient algorithm, a cross correlation score algorithm, a clustering algorithm, an entropy minimization algorithm, a Dot product score algorithm and a minimum spanning tree algorithm.

15. The method of claim 1, wherein the data post-processing further comprises: performing charge number deconvolution on the mass spectrum to determine a charge number corresponding to a mass spectrum peak.

16. A device for parallel analysis in mass spectrometry and ion mobility spectrometry, comprising:
a chromatograph;
an ion mobility spectrometer located at a succeeding stage of the chromatograph;
a mass spectrometer located at a succeeding stage of the chromatograph; and
a computer connected to the ion mobility spectrometer and the mass spectrometer,
wherein a sample is subjected to a chromatography separation; the chromatography separated sample is ionized and then fed into a succeeding stage device for analysis, comprising: analyzing at least part of the ionized sample through an ion mobility spectrometer to obtain an ion mobility spectrum, and analyzing at least other parts of the sample through a mass spectrometer to obtain a mass spectrum, wherein the period for obtaining each ion mobility spectrum and each mass spectrum being not longer than 5 s; the computer performs data post-processing, comprising: correlating the peaks in said ion mobility spectrum and the peaks in said mass spectrum with a deconvolution algorithm according to the consistency in retention time or elution profile for the same analyte in said chromatograph.

17. The device of claim 16, further comprising at least one switching valve, connected to the chromatograph, wherein, the chromatography separated sample is divided into two paths by the switching valve before the ionization, and said two paths of samples are then ionized and respectively fed to the ion mobility spectrometer and the mass spectrometer for analysis.

18. The device of claim 16, further comprising two different ion inlets respectively connected to the ion mobility spectrometer and the mass spectrum analyzer, wherein the chromatography separated sample is ionized, and generated ions are respectively transmitted to the ion mobility spectrometer and the mass spectrometer through two different ion inlets.

19. The device of claim 16, further comprising an ion optical device, wherein the chromatography separated sample is ionized, and generated ions pass through the ion optical device, wherein said ion optical device periodically alternately feeds said ions to the ion mobility spectrometer and the mass spectrometer for analysis.

20. The device of claim 16, wherein the chromatography separated sample is ionized, and generated ions are separated by the ion mobility spectrometer and then are analyzed by the mass spectrometer.

21. The device of claim 16, wherein the chromatograph is a gas chromatograph, a liquid chromatograph, a supercritical fluid chromatograph, an ion chromatograph or a capillary electrophoresis apparatus.

22. The device of claim 16, wherein the ion mobility spectrometer is a drift tube ion mobility spectrometer, a differential ion mobility spectrometer or a high-field asymmetric waveform ion mobility spectrometer (FAIMS).

23. The device of claim 16, wherein the mass analyzer of the mass spectrometer is a quadrupole mass filter or an ion trap mass analyzer, or a Fourier transform ion cyclotron resonance mass analyzer or an Orbitrap mass analyze.

24. The device of claim 16, wherein the mass analyzer of the mass spectrometer is a time-of-flight mass analyzer.

25. The device of claim 16, wherein the mass spectrometer is a tandem mass spectrometer containing a collision cell.

26. The device of claim 25, wherein the chromatography separated sample is ionized, and generated ions enter the collision cell for collisional dissociation, and then pass through an ion optical device, wherein said ion optical device periodically alternately feeds said ions to the ion mobility spectrometer and the mass spectrometer for analysis.

27. The device of claim 25, wherein after the chromatography separation and ionization for sample, and then being collisional dissociated in said collision cell, the generated ions are separated by the ion mobility analyzer in the ion mobility spectrometer, and then enter the mass analyzer in the mass spectrometer for mass analysis.

28. The device of claim 25, wherein after the chromatography separation and ionization for sample, the generated ions are separated by the ion mobility analyzer in the ion mobility spectrometer, then enter the collision cell for collisional dissociation, and then the generated ions enter the mass analyzer in the mass spectrometer for mass analysis.

29. The device of claim 16, wherein the deconvolution algorithm is one or a combination of more of a Pearson's correlation coefficient algorithm, a cross correlation score algorithm, a clustering algorithm, an entropy minimization algorithm, a Dot product score algorithm and a minimum spanning tree algorithm.

30. The device of claim 16, wherein the data post-processing further comprises: performing charge number deconvolution on the mass spectrum to determine a charge number corresponding to a mass spectrum peak.

* * * * *